(12) United States Patent
Cheng et al.

(10) Patent No.: US 7,291,166 B2
(45) Date of Patent: Nov. 6, 2007

(54) POLYMERIC STENT PATTERNS

(75) Inventors: E. Tina Cheng, Union City, CA (US); Rosabel Chang, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 339 days.

(21) Appl. No.: 11/132,758

(22) Filed: May 18, 2005

(65) Prior Publication Data

US 2006/0265048 A1 Nov. 23, 2006

(51) Int. Cl.
*A61F 2/06* (2006.01)
(52) U.S. Cl. .................................... 623/1.15
(58) Field of Classification Search ....... 623/1.11–1.22
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |

(Continued)

FOREIGN PATENT DOCUMENTS

DE 44 07 079 9/1994

(Continued)

OTHER PUBLICATIONS

U.S. Appl. No. 10/317,435, filed Dec. 11, 2002, Hossainy et al.

(Continued)

*Primary Examiner*—Suzette Gherbi
(74) *Attorney, Agent, or Firm*—Squire, Sanders & Demsey, LLP

(57) ABSTRACT

Patterns for polymeric radially expandable implantable medical devices such as stents for implantation into a bodily lumen are disclosed. Some patterns comprise radially expandable cylindrical rings that are longitudinally aligned, each ring comprising diamond-shaped elements, each formed by four linear bar arms. The patterns con also comprise a cross-like element comprising four linear bar arms interconnected within the diamond-shaped elements, and at least one link between adjacent rings. In other patterns, the rings comprise peaks and valleys formed by linear bar arms. wherein pairs of rings are configured such that the peaks of one pair are connected to the valleys of the other pair at apices of the peaks and valleys to form diamond shaped regions. In yet other patterns, there are two v-shaped elements formed by two short bar arms within the diamond-shaped elements, and a connecting bar arm connecting the two v-shaped elements.

21 Claims, 12 Drawing Sheets

U.S. PATENT DOCUMENTS

| | | |
|---|---|---|
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |

| | | | | | | |
|---|---|---|---|---|---|---|
| 5,948,428 A | 9/1999 | Lee et al. | 6,379,381 B1 | 4/2002 | Hossainy et al. | |
| 5,954,744 A | 9/1999 | Phan et al. | 6,387,121 B1 | 5/2002 | Alt | |
| 5,957,975 A | 9/1999 | Lafont et al. | 6,388,043 B1 | 5/2002 | Langer et al. | |
| 5,965,720 A | 10/1999 | Gryaznov et al. | 6,395,326 B1 | 5/2002 | Castro et al. | |
| 5,971,954 A | 10/1999 | Conway et al. | 6,409,761 B1 | 6/2002 | Jang | |
| 5,976,182 A | 11/1999 | Cox | 6,423,092 B2 | 7/2002 | Datta et al. | |
| 5,980,564 A | 11/1999 | Stinson | 6,436,132 B1 * | 8/2002 | Patel et al. | 623/1.13 |
| 5,980,928 A | 11/1999 | Terry | 6,461,632 B1 | 10/2002 | Gogolewski | |
| 5,980,972 A | 11/1999 | Ding | 6,464,720 B2 | 10/2002 | Boatman et al. | |
| 5,981,568 A | 11/1999 | Kunz et al. | 6,479,565 B1 | 11/2002 | Stanley | |
| 5,986,169 A | 11/1999 | Gjunter | 6,485,512 B1 | 11/2002 | Cheng | |
| 5,997,468 A | 12/1999 | Wolff et al. | 6,492,615 B1 | 12/2002 | Flanagan | |
| 6,010,445 A | 1/2000 | Armini et al. | 6,494,908 B1 | 12/2002 | Huxel et al. | |
| 6,015,541 A | 1/2000 | Greff et al. | 6,495,156 B2 | 12/2002 | Wenz et al. | |
| 6,042,875 A | 3/2000 | Ding et al. | 6,511,748 B1 | 1/2003 | Barrows | |
| 6,048,964 A | 4/2000 | Lee et al. | 6,517,888 B1 | 2/2003 | Weber | |
| 6,051,648 A | 4/2000 | Rhee et al. | 6,527,801 B1 | 3/2003 | Dutta | |
| 6,056,993 A | 5/2000 | Leidner et al. | 6,537,589 B1 | 3/2003 | Chae et al. | |
| 6,060,451 A | 5/2000 | DiMaio et al. | 6,539,607 B1 | 4/2003 | Fehring et al. | |
| 6,066,156 A | 5/2000 | Yan | 6,540,777 B2 | 4/2003 | Stenzel | |
| 6,071,266 A | 6/2000 | Kelley | 6,554,854 B1 | 4/2003 | Flanagan | |
| 6,074,659 A | 6/2000 | Kunz et al. | 6,565,599 B1 | 5/2003 | Hong et al. | |
| 6,080,177 A | 6/2000 | Igaki et al. | 6,569,191 B1 | 5/2003 | Hogan | |
| 6,080,488 A | 6/2000 | Hostettler et al. | 6,569,193 B1 | 5/2003 | Cox et al. | |
| 6,083,258 A | 7/2000 | Yadav | 6,572,649 B2 * | 6/2003 | Berry et al. | 623/1.15 |
| 6,093,463 A | 7/2000 | Thakrar | 6,572,672 B2 | 6/2003 | Yadav et al. | |
| 6,096,070 A | 8/2000 | Ragheb et al. | 6,574,851 B1 | 6/2003 | Mirizzi | |
| 6,096,525 A | 8/2000 | Patnaik | 6,585,755 B2 | 7/2003 | Jackson et al. | |
| 6,099,562 A | 8/2000 | Ding et al. | 6,592,614 B2 | 7/2003 | Lenker et al. | |
| 6,103,230 A | 8/2000 | Billiar et al. | 6,592,617 B2 | 7/2003 | Thompson | |
| 6,107,416 A | 8/2000 | Patnaik et al. | 6,613,072 B2 | 9/2003 | Lau et al. | |
| 6,110,188 A | 8/2000 | Narciso, Jr. | 6,626,939 B1 | 9/2003 | Burnside et al. | |
| 6,113,629 A | 9/2000 | Ken | 6,635,269 B1 | 10/2003 | Jennissen | |
| 6,117,979 A | 9/2000 | Hendriks et al. | 6,645,243 B2 | 11/2003 | Vallana et al. | |
| 6,120,536 A | 9/2000 | Ding et al. | 6,656,162 B2 | 12/2003 | Santini, Jr. et al. | |
| 6,120,904 A | 9/2000 | Hostettler et al. | 6,664,335 B2 | 12/2003 | Krishnan | |
| 6,121,027 A | 9/2000 | Clapper et al. | 6,666,214 B2 | 12/2003 | Canham | |
| 6,125,523 A | 10/2000 | Brown et al. | 6,667,049 B2 | 12/2003 | Janas et al. | |
| 6,127,173 A | 10/2000 | Eckstein et al. | 6,669,723 B2 | 12/2003 | Killion et al. | |
| 6,129,761 A | 10/2000 | Hubbell | 6,676,697 B1 | 1/2004 | Richter | |
| 6,129,928 A | 10/2000 | Sarangapani et al. | 6,679,980 B1 | 1/2004 | Andreacchi | |
| 6,150,630 A | 11/2000 | Perry et al. | 6,689,375 B1 | 2/2004 | Wahlig et al. | |
| 6,153,252 A | 11/2000 | Hossainy et al. | 6,695,920 B1 | 2/2004 | Pacetti et al. | |
| 4,776,337 A | 12/2000 | Palmaz | 6,706,273 B1 | 3/2004 | Roessler | |
| 6,159,951 A | 12/2000 | Karpeisky et al. | 6,709,379 B1 | 3/2004 | Brandau et al. | |
| 6,160,084 A | 12/2000 | Langer et al. | 6,719,934 B2 | 4/2004 | Stinson | |
| 6,165,212 A | 12/2000 | Dereume et al. | 6,719,989 B1 | 4/2004 | Matsushima et al. | |
| 6,166,130 A | 12/2000 | Rhee et al. | 6,720,402 B2 | 4/2004 | Langer et al. | |
| 6,169,170 B1 | 1/2001 | Gryaznov et al. | 6,746,773 B2 | 6/2004 | Llanos et al. | |
| 6,171,609 B1 | 1/2001 | Kunz | 6,752,826 B2 | 6/2004 | Holloway et al. | |
| 6,174,330 B1 | 1/2001 | Stinson | 6,753,007 B2 | 6/2004 | Haggard et al. | |
| 6,177,523 B1 | 1/2001 | Reich et al. | 6,764,505 B1 | 7/2004 | Hossainy et al. | |
| 6,183,505 B1 | 2/2001 | Mohn, Jr. et al. | 6,818,063 B1 | 11/2004 | Kerrigan | |
| 6,187,045 B1 | 2/2001 | Fehring et al. | 6,846,323 B2 | 1/2005 | Yip et al. | |
| 6,210,715 B1 | 4/2001 | Starling et al. | 2001/0044652 A1 | 11/2001 | Moore | |
| 6,224,626 B1 | 5/2001 | Steinke | 2002/0002399 A1 | 1/2002 | Huxel et al. | |
| 6,228,845 B1 | 5/2001 | Donovan et al. | 2002/0004060 A1 | 1/2002 | Heublein et al. | |
| 6,240,616 B1 | 6/2001 | Yan | 2002/0004101 A1 | 1/2002 | Ding et al. | |
| 6,245,076 B1 | 6/2001 | Yan | 2002/0062148 A1 | 5/2002 | Hart | |
| 6,245,103 B1 | 6/2001 | Stinson | 2002/0065553 A1 | 5/2002 | Weber | |
| 6,248,344 B1 | 6/2001 | Ylanen et al. | 2002/0111590 A1 | 8/2002 | Davila et al. | |
| 6,251,135 B1 | 6/2001 | Stinson et al. | 2002/0116050 A1 | 8/2002 | Kocur | |
| 6,251,142 B1 | 6/2001 | Bernacca et al. | 2002/0138133 A1 | 9/2002 | Lenz et al. | |
| 6,273,913 B1 | 8/2001 | Wright et al. | 2002/0161114 A1 | 10/2002 | Gunatillake et al. | |
| 6,281,262 B1 | 8/2001 | Shikinami | 2003/0033001 A1 | 2/2003 | Igaki | |
| 6,284,333 B1 | 9/2001 | Wang et al. | 2003/0093107 A1 | 5/2003 | Parsonage et al. | |
| 6,287,332 B1 | 9/2001 | Bolz et al. | 2003/0100865 A1 | 5/2003 | Santini, Jr. et al. | |
| 6,290,721 B1 | 9/2001 | Heath | 2003/0105518 A1 | 6/2003 | Dutta | |
| 6,293,966 B1 | 9/2001 | Frantzen | 2003/0105530 A1 | 6/2003 | Pirhonen | |
| 6,303,901 B1 | 10/2001 | Perry et al. | 2003/0171053 A1 | 9/2003 | Sanders | |
| 6,312,459 B1 | 11/2001 | Huang et al. | 2003/0187495 A1 | 10/2003 | Cully et al. | |
| 6,327,772 B1 | 12/2001 | Zadno-Azizi et al. | 2003/0208259 A1 | 11/2003 | Penhasi | |
| 6,375,826 B1 | 4/2002 | Wang et al. | 2003/0209835 A1 | 11/2003 | Chun et al. | |

| | | | |
|---|---|---|---|
| 2003/0226833 | A1 | 12/2003 | Shapovalov et al. |
| 2003/0236565 | A1 | 12/2003 | Fifer |
| 2004/0093077 | A1 | 5/2004 | White et al. |
| 2004/0098095 | A1 | 5/2004 | Burnside et al. |
| 2004/0111149 | A1 | 6/2004 | Stinson |
| 2004/0127970 | A1 | 7/2004 | Weber |
| 2004/0143317 | A1 | 7/2004 | Stinson et al. |
| 2004/0167610 | A1 | 8/2004 | Fleming III |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO89/03232 | 4/1989 |
| WO | WO90/01969 | 3/1990 |
| WO | WO90/04982 | 5/1990 |
| WO | WO90/06094 | 6/1990 |
| WO | WO91/17744 | 11/1991 |
| WO | WO91/17789 | 11/1991 |
| WO | WO92/10218 | 6/1992 |
| WO | WO93/06792 | 4/1993 |
| WO | WO94/21196 | 9/1994 |
| WO | WO95/29647 | 11/1995 |
| WO | WO98/04415 | 2/1998 |
| WO | WO99/03515 | 1/1999 |
| WO | WO99/16386 | 4/1999 |
| WO | WO99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.
Ansari, *Tubal Reanastomosis Using Absorbable Stent*, International Journal of Fertility, vol. 23, No. 4, pp. 242-243 (1978).
Ansari, *End-to-end tubal anastomosis using an absorbable stent*, Fertility and Sterility, vol. 32(2), pp. 197-201 (Aug. 1979).
Bull, *Parylene Coating for Medical Applications*, Medical Product Manufacturing News 1 pg. (Mar. 1993).
Casper et al., *Fiber-Reinforced Absorbable Composite for Orthopedic Surgery*, Polymeric Materials Science and Engineering, 53: pp. 497-501 (1985).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Feng-Chun et al., *Assessment of Tissue Blood Flow Following Small Artery Welding with an Intraluminal Dissolvable Stent*, Microsurgery, vol. 19(3), pp. 148-152 (1999).
Hahn et al., *Glow Discharge Polymers as Coatings for Implanted Devices*, ISA, pp. 109-111 (1981).
Hahn et al., *Biocompatibility of Glow-Discharge-Polymerized Films and Vacuum-Deposited Parylene*, J Applied Polymer Sci, 38, pp. 55-64 (1984).
Kelley et al., *Totally Resorbable High-Strength Composite Material*, Advances in Biomedical Polymers, 35, pp. 75-85 (1987).
Kubies et al., *Microdomain Structure In polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents 16 pgs. (1999).
Mauduit et al., *Hydrolytic degradation of films prepared from blends of high and low molecular weight poly(DL-lactic acid)s*, J. Biomed. Mater. Res. v. 30, pp. 201-207 (1996).
Martin et al., *Enhancing the biological activity of immobilized osteopontin using a type-1 collagen affinity coating*, J. Biomed. Mater Res 70A, pp. 10-19 (2004).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degrabable cardiovascular stents produced from corrodible metal-results 6-18 months after implantation into New Zealand white rabbits*, Heart 86, pp. 563-569 (2001).
Pietrzak et al., *Bioresorbable implants—practical considerations*, Bone v. 19, No. 1, Supplement Jul. 1996: 109s-119s.
Pietrzak et al., *Bioabsorbable Fixation Devices: Status for the Craniomaxillofacial Surgeon*, J. Craniofaxial Surg. 2, pp. 92-96 (1997).
von Recum et al., *Degradation of polydispersed poly(L-lactic acid) to modulate lactic acid release*, Biomaterials 16, pp. 441-445 (1995).
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-I-Lactic Acid Coronary Stents in Humans*, Circulation, pp. 399-404 (2000).
Tsui et al., *Biodegradable Polymeric Stents*, Current Interventional Cardiology Reports 3, pp. 10-17 (2001).
Völkel et al., *Targeting of immunoliposomes to endothelial cells using a single—chain Fv fragment directed against human endoglin (CD105)*, Biochemica et Biophysica Acta 1663, pp. 158-166 (2004).
Yau et al., Modern Size-Exclusion Liquid Chromatography, Wiley-Interscience Publication, (1979).

* cited by examiner

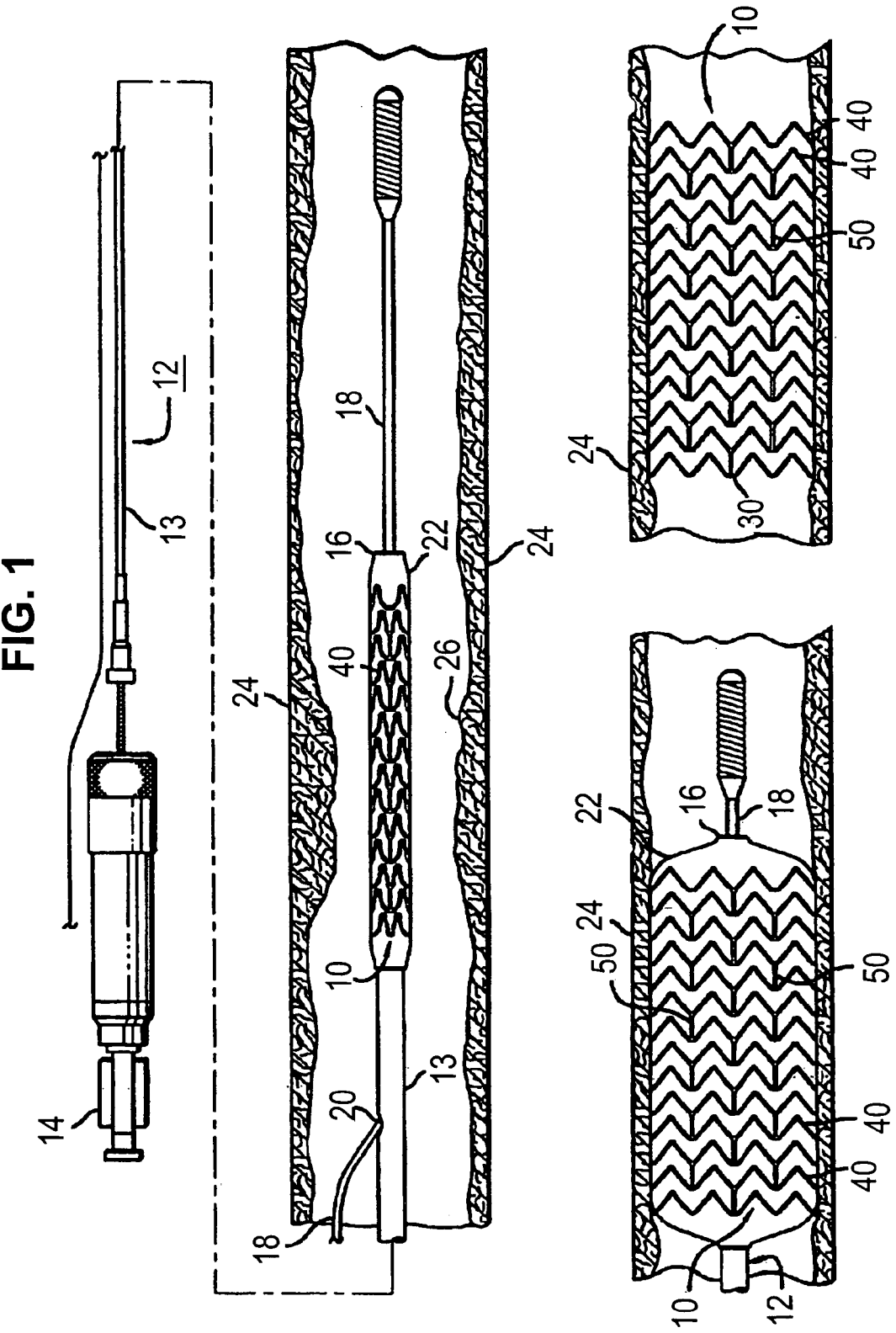

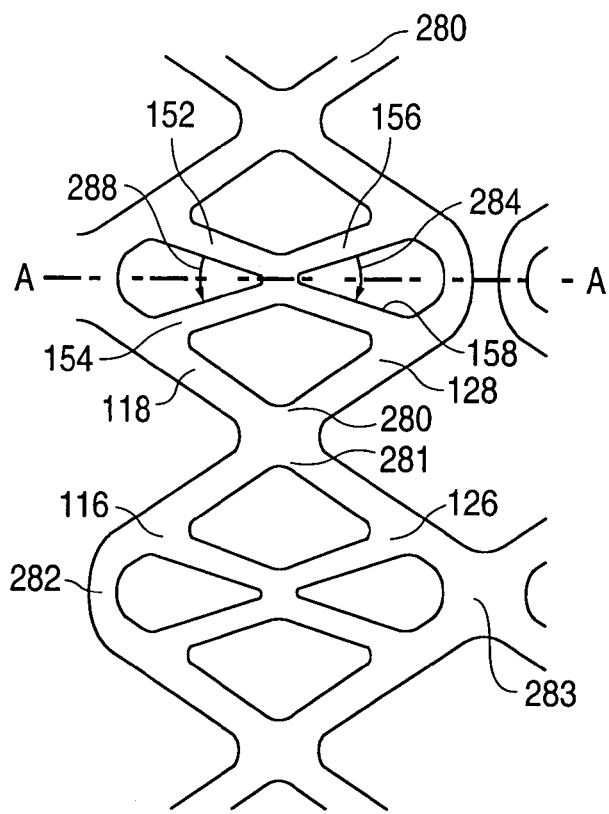
FIG. 8B
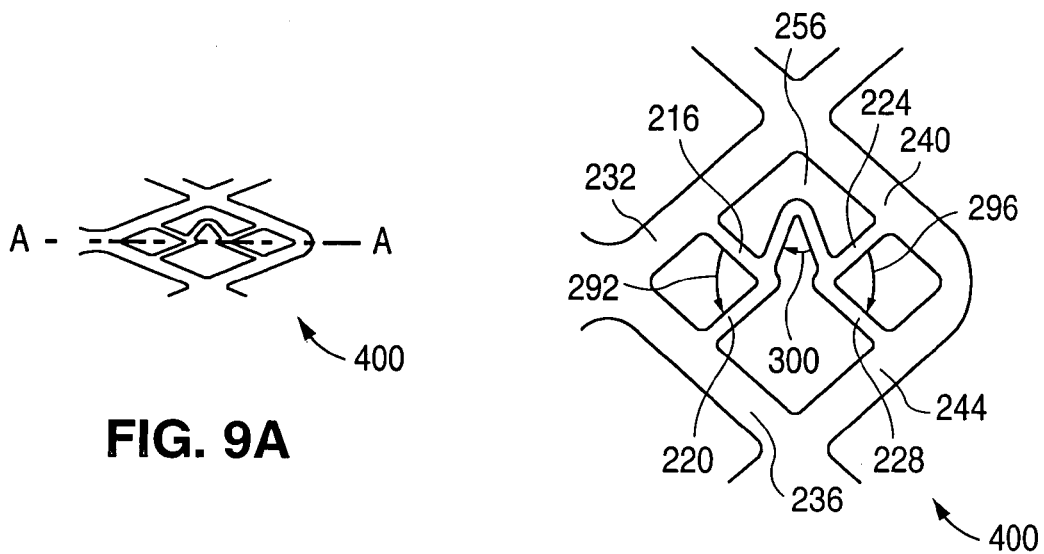
FIG. 9A
FIG. 9B

POLYMERIC STENT PATTERNS

BACKGROUND OF THE INVENTION

1. Field of the Invention

This invention relates to radially expandable implantable medical devices such as stents for implantation into a bodily lumen. In particular, the invention relates to stent patterns for polymeric stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other. Thus, a stent pattern may be designed to meet the mechanical requirements of a stent described above which include radial strength, minimal recoil, plaque support, and flexibility.

Stents have been made of many materials such as metals and polymers, including biodegradable polymeric materials. Biodegradable stents are desirable in many treatment applications in which the presence of a stent in a body may be necessary for a limited period of time until its intended function of, for example, achieving and maintaining vascular patency and/or drug delivery is accomplished. A stent for drug delivery or a medicated stent may be fabricated by coating the surface of either a metallic or polymeric scaffolding with a polymeric carrier that includes an active agent or drug. An agent or drug may also be mixed or dispersed within the polymeric scaffolding.

In general, there are several important aspects in the mechanical behavior of polymers that affect stent design. Polymers tend to have lower strength than metals on a per unit mass basis. Therefore, polymeric stents typically have less circumferential strength and radial rigidity than metallic stents of the same or similar dimensions. Inadequate radial strength potentially contributes to a relatively high incidence of recoil of polymeric stents after implantation into vessels.

Another potential problem with polymeric stents is that their struts or bar arms can crack during crimping and expansion, especially for brittle polymers. The localized portions of the stent pattern subjected to substantial deformation tend to be the most vulnerable to failure. Furthermore, in order to have adequate mechanical strength, polymeric stents may require significantly thicker struts than a metallic stent, which results in an undesirably larger profile.

Another potential problem with polymeric stents is long term creep. Long term creep is typically not an issue with metallic stents. Long term creep refers to the gradual deformation that occurs in a polymeric material subjected to an applied load. Long term creep occurs even when the applied load is constant. Long term creep in a polymeric stent reduces the effectiveness of a stent in maintaining a desired vascular patency. In particular, long term creep allows inward radial forces to permanently deform a stent radially inward.

Therefore, it would be desirable to have polymeric stents with stent patterns that provide adequate radial strength, minimal recoil, plaque support, and flexibility.

SUMMARY OF THE INVENTION

Certain embodiments of the present invention include a radially expandable intravascular stent for implanting in a bodily lumen that may include a plurality of radially expandable cylindrical rings that are longitudinally aligned. Each ring may have a first delivery diameter and a second implanted diameter. Each ring may further include a plurality of diamond-shaped elements formed by four linear bar arms, wherein adjacent elements on the ring are connected at apices of the adjacent elements. The stent may also include a cross-like element comprising four linear bar arms interconnected within at least one diamond-shaped element, wherein one end of each bar arm of the cross-like element is connected to one of the bar arms of the at least one diamond-shaped element between two adjacent apices of the at least one diamond-shaped element. The stent may additionally include at least one link between adjacent rings, wherein the at least one link connects longitudinal apices of adjacent diamond-shaped elements of adjacent rings.

Other embodiments of the present invention may also include a radially expandable intravascular stent for implanting in a bodily lumen having a plurality of pairs of radially expandable undulating cylindrical rings that are longitudinally aligned comprising peaks and valleys formed by linear bar arms, wherein the pairs of rings are configured such that the peaks of one pair are connected to the valleys of the other pair at apices of the peaks and valleys to form a plurality of diamond shaped regions. The stent may further include at least one link between adjacent rings, wherein the at least one link connects a peak on one ring to an adjacent valley on an adjacent ring. The stent may also include a cross-like element comprising four linear bar arms interconnected within at least one diamond-shaped element, wherein one end of each bar arm of the cross-like element is connected to one of the linear bar arms of the rings between a peak and a valley of the ring and another end of each bar arm interconnected to ends of the bar arms of the cross-like element.

Additional embodiments of the present invention may include a radially expandable intravascular stent for implanting in a bodily lumen having a plurality of radially expandable cylindrical rings that are longitudinally aligned with each ring including a first delivery diameter and a second implanted diameter, and a plurality of diamond-shaped elements formed by four linear bar arms, wherein adjacent elements on the ring are connected at apices of the adjacent elements. The stent may also include at least one link between adjacent rings, wherein the at least one link connects longitudinal apices of adjacent diamond-shaped elements of adjacent rings. The stent may further include two v-shaped elements formed by two short bar arms within at least one diamond-shaped element, ends of the short bar arms of one v-shaped element are connected to bar arms of the diamond-shaped element on either side of one longitudinal apex of the diamond-shaped element, and ends the short bar arms of a second v-shaped element are connected to bar arms of the diamond-shaped element on either side of a second longitudinal apex of the diamond-shaped element. The stent may additionally include a connecting bar arm within at least one diamond-shaped element connecting the apices of the two v-shaped elements.

Further embodiments of the present invention may include a radially expandable intravascular stent for implanting in a bodily lumen having a plurality of pairs of radially expandable undulating cylindrical rings that are longitudinally aligned comprising peaks and valleys formed by linear bar arms, wherein the pairs of rings are configured such that the peaks of one pair are connected to the valleys of the other pair at apices of the peaks and valleys to form a plurality of diamond shaped regions. The stent may also include at least one link between adjacent rings, wherein the at least one link connects a peak on one ring to an adjacent valley on an adjacent ring. The may further include two v-shaped elements formed by two short bar arms within at least one diamond-shaped element, ends of the short bar arms of one v-shaped element are connected to bar arms of the diamond-shaped element on either side of one longitudinal apex of the diamond-shaped element, and ends the short bar arms of a second v-shaped element are connected to bar arms of the diamond-shaped element on either side of a second longitudinal apex of the diamond-shaped element. The stent may additionally include a connecting bar arm within at least one diamond-shaped element connecting the apices of the two v-shaped elements.

Additional embodiment of the present invention may include a radially expandable intravascular stent for implanting in a bodily lumen having a plurality of radially expandable cylindrical rings that are longitudinally aligned, each ring having a first delivery diameter and a second implanted diameter and a plurality of diamond-shaped elements formed by four linear bar arms, wherein adjacent elements on the ring are connected at apices of the adjacent elements. The stent may also include two connecting elements within at least one diamond-shaped element with each element having two ends, the ends of one connecting element are connected to bar arms of the diamond-shaped element on either side of one longitudinal apex of the diamond-shaped element, and the ends of a second connecting element are connected to bar arms of the diamond-shaped element on either side of a second longitudinal apex of the diamond-shaped element. The stent may further include a connecting bar arm within at least one diamond-shaped element connecting the two connecting elements. The stent may additionally include at least one link between adjacent rings, wherein the at least one link connects longitudinal apices of adjacent diamond-shaped elements of adjacent rings.

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

FIG. 8B depicts a portion of the stent pattern of FIG. 5 in an expanded state.

FIG. 9A depicts a portion of the stent pattern of FIG. 7A in an unexpanded state.

FIG. 9B depicts a portion of the stent pattern of FIG. 7A in an expanded state.

DETAILED DESCRIPTION OF THE INVENTION

Figure 4:
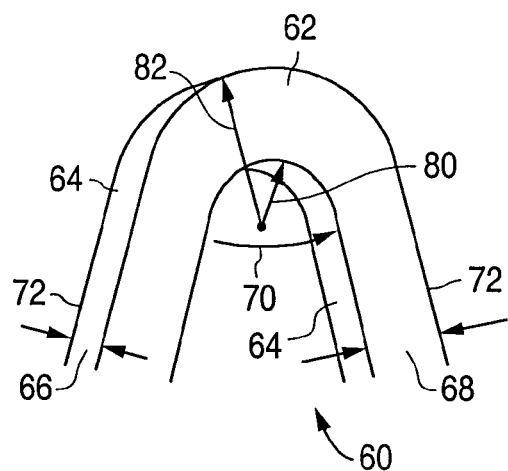
FIG. 4 depicts a curved portion of a stent.

For the purposes of the present invention, the following terms and definitions apply:

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of strain with applied stress is the modulus. "Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its $T_g$, a polymer tends to be brittle with a high modulus. As the temperature of a polymer is increased from below to above its $T_g$, its modulus decreases.

The "ultimate strength" or "strength" of a material refers to the maximum stress that a material will withstand prior to fracture. A material may have both a tensile and a compressive strength. The ultimate strength may be calculated from the maximum load applied during a test divided by the original cross-sectional area.

The term "elastic deformation" refers to deformation of an object in which the applied stress is small enough so that the object moves towards its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation.

"Elastic limit" refers to the maximum stress that a material will withstand without permanent deformation. The "yield point" is the stress at the elastic limit and the "ultimate strain" is the strain at the elastic limit. The term "plastic deformation" refers to permanent deformation that occurs in a material under stress after elastic limits have been exceeded.

Various embodiments of stent patterns for polymeric stents are disclosed herein. Stents may be composed partially or completely of polymers. In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body. In addition, a medicated stent may be fabricated by coating the surface of the stent with an active agent or drug, or a polymeric carrier including an active agent or drug.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration is typically in the range of six to eighteen months.

The general structure and use of stents will be discussed first in order to lay a foundation for the embodiments of stent patterns herein. In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility.

FIGS. 1-3 can represent any balloon expandable stent 10 with which the various configurations can be used. FIG. 1 depicts a stent 10 with interconnected cylindrical rings 40 mounted on a catheter assembly 12 which is used to deliver stent 10 and implant it in a body lumen. Rings 40 are connected by links 50.

For example, a bodily lumen may include a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1-3 conceptually represents any type of stent well-known in the art, i.e., one having a plurality of rings 40.

Catheter assembly 12, as depicted in FIG. 1, includes an RX (rapid-exchange) port 20 where the guide wire 18 exits the catheter. The distal end of guide wire 18 exits catheter distal end 16 so that the catheter advances along the guide wire on a section of the catheter between RX port 20 and catheter distal end 16. As is known in the art, the guide wire lumen which receives the guide wire is sized for receiving various diameter guide wires to suit a particular application. The stent is mounted on an expandable member 22 (e.g., a balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other vessels. Stent 10, and embodiments of the stents described herein, also can be placed and implanted without any prior angioplasty.

In a typical procedure to implant stent 10, guide wire 18 is advanced through the patient's vascular system by well-known methods, so that the distal end of the guide wire is advanced past the plaque or a diseased area 26. Prior to implanting the stent, the cardiologist may wish to perform an angioplasty or other procedure (i.e., atherectomy) in order to open and remodel the vessel and the diseased area. Thereafter, stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall. In FIG. 3, the implanted stent remains in the vessel after the balloon has been deflated and the catheter assembly and guide wire have been withdrawn from the patient.

Stent 10 holds open the artery after the catheter is withdrawn, as illustrated by FIG. 3. A stent may be formed from a cylindrical tube with a constant wall thickness, so that the straight and undulating or curved components of the stent are relatively flat in transverse cross-section. Thus, when the stent is expanded, a flat abluminal surface is pressed into the wall of the artery. As a result, the stent does not interfere with the blood flow through the artery. After the stent is pressed into the wall of the artery, it eventually becomes covered with endothelial cell growth which further minimizes blood flow interference. The undulating or curved portion of the stent provides good tacking characteristics to prevent stent movement within the artery. Because cylindrical rings 40 are closely spaced at regular intervals, they provide uniform support for the wall of the artery. Consequently the rings are well adapted to tack up and hold in place small flaps or dissections in the wall of the artery.

In general, a stent pattern is designed so that the stent can be radially expanded (to allow deployment). The stresses involved during expansion from a low profile to an expanded profile are generally distributed throughout various structural elements of the stent pattern. As a stent expands, various portions of the stent can deform to accomplish a radial expansion.

FIG. 4 depicts a curved portion 60 of a stent. Portion 60 has an abluminal surface 62 and an opposing luminal surface (not shown). Sidewall surfaces 64 are also shown. Portion 60 has a radial thickness 66 and a strut width 68. Stent patterns typically have a constant radial thickness throughout the pattern because stents are typically fabricated from tubes of sheets of uniform or substantially uniform thickness. When a stent undergoes radial expansion, portions of some struts bend resulting in an increase of an angle 70 between straight bar arms 72. In addition, the degree of bending of curved portion 60 can be defined by an inner radius 80 and an outer radius 82. Inner radius 80 and outer radius 82 are shown to be concentric, however, they may also be non-concentric.

The stiffness or flexibility of a portion of a stent pattern can depend on the mass of the portion of the stent. The mass of a portion may be varied by varying the width and/or length of a strut or bar arm that makes up the portion. The shorter a strut, the less stiff and more deformable along its length it is. Similarly, the smaller the width of a stent, the less stiff and more deformable along its length it is. Therefore, a portion with a smaller mass may tend to undergo more deformation for a give amount of applied force. By allocating the amount of mass to specific struts, it is possible to create a stent having variable strength with greater strength at the high mass areas.

In addition to the stent pattern, the chemical and mechanical properties of a polymeric material making up a stent may influence a stent's radial strength, recoil, and flexibility. Deformation of portions of a stent during radial expansion may induce crystallization and/or circumferential molecular orientation along the axis of stress. This process is referred to as strain-induced crystallization. As discussed above, induced crystallization and orientation tend to increase the mechanical strength and rigidity of tube-like section along the direction of orientation of the polymer chains. Therefore, the radial strength and rigidity of a tube-like section may be increased by expansion of the device.

Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress which results in an oriented crystalline structure. Thus, strain-induced crystallization in portions of a stent may result in a permanent increase in strength and modulus in that portion. This is particularly advantageous since after expansion in a lumen, it is generally desirable for a stent to remain rigid and maintain its expanded shape so that it may continue to hold open the lumen.

Furthermore, induced orientation and crystallization of a portion of a stent may increase a $T_g$ of at least a deformed portion. The $T_g$ of the polymer in the device may be increased to above body temperature. Therefore, barriers to polymer chain mobility below $T_g$ may tend to inhibit or prevent loss of induced orientation and crystallization. Thus, a deformed portion may have a high creep resistance and may more effectively resist radial compressive forces and retain the expanded shape during a desired time period.

When a stent undergoes expansion, for example, the deformation in localized portions can result in strain-induced crystallization. Therefore, the localized portions may have a higher strength and modulus after expansion. Additionally, plastic deformation causes the portions to be "locked" in the deformed state. Also, the more the deformation is aligned circumferentially, then the greater the radial strength of the expanded stent due to the strain induced crystallization of the localized portions.

Figure 5:
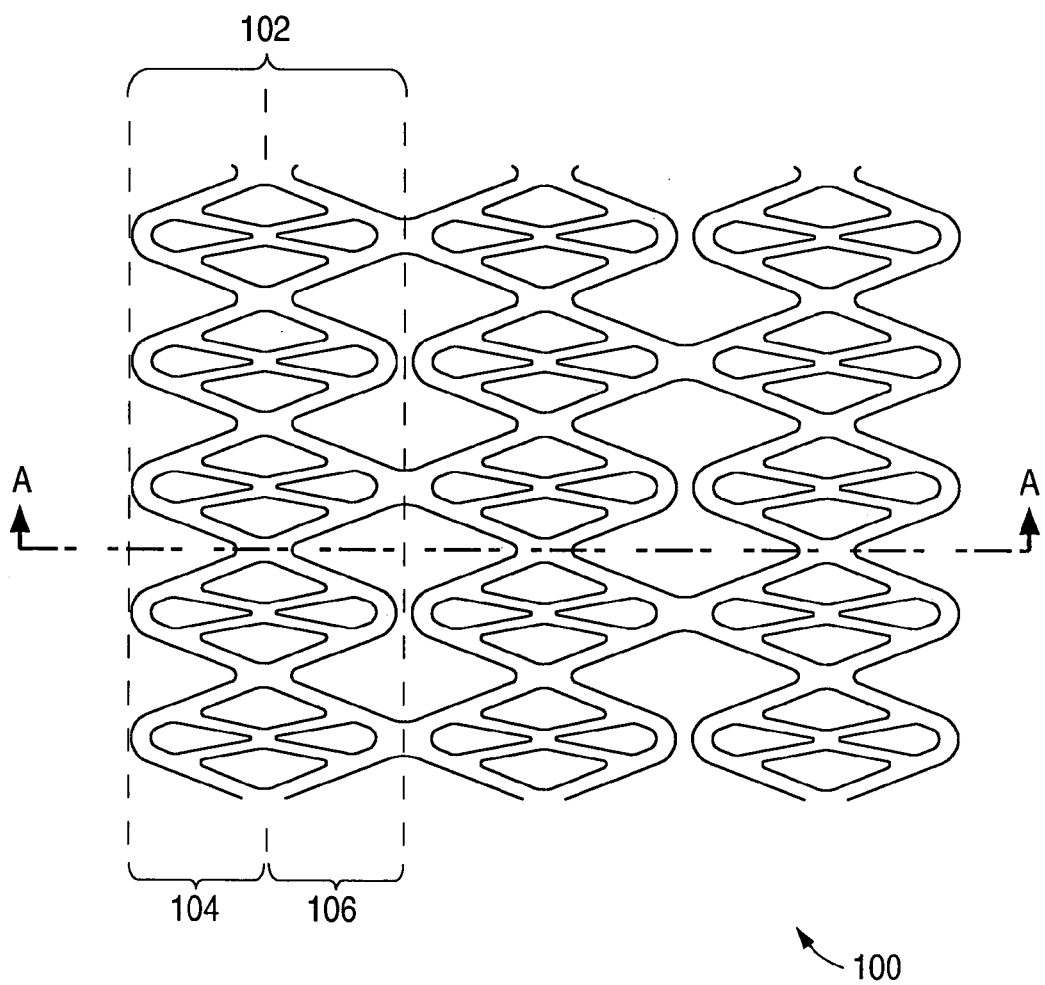
FIG. 5 depicts a stent pattern.

FIG. 5 depicts one embodiment of a stent pattern. In FIG. 5, a portion of a stent pattern 100 is shown in a flattened condition so that the pattern can be clearly viewed. When the flattened portion of stent pattern 100 is in a cylindrical condition, it forms a stent. The stent is typically formed from a tubular member, but it can be formed from a flat sheet, such as the portion shown in FIG. 5, and rolled into a cylindrical configuration.

Stent 100 in FIG. 5 can include a plurality of pairs 102 of radially expandable undulating cylindrical rings 104 and 106 with crests including peaks and valleys that are longitudinally aligned. Embodiments of stent 100 may have any number of pairs 102 of rings. For reference, line A-A represents the longitudinal axis of a stent using the pattern depicted in FIG. 5. A portion of stent 100 in FIG. 5 is shown in greater detail for greater ease of illustration in FIG. 6.

The selection of which crest is a peak and which crest is a valley is arbitrary and done for ease of reference. Those in the art will understand that, depending upon one's reference, a peak can be a valley, and vice versa. Moreover, those in the art will understand from context the meanings of peak, valley and crest.

Figure 6:
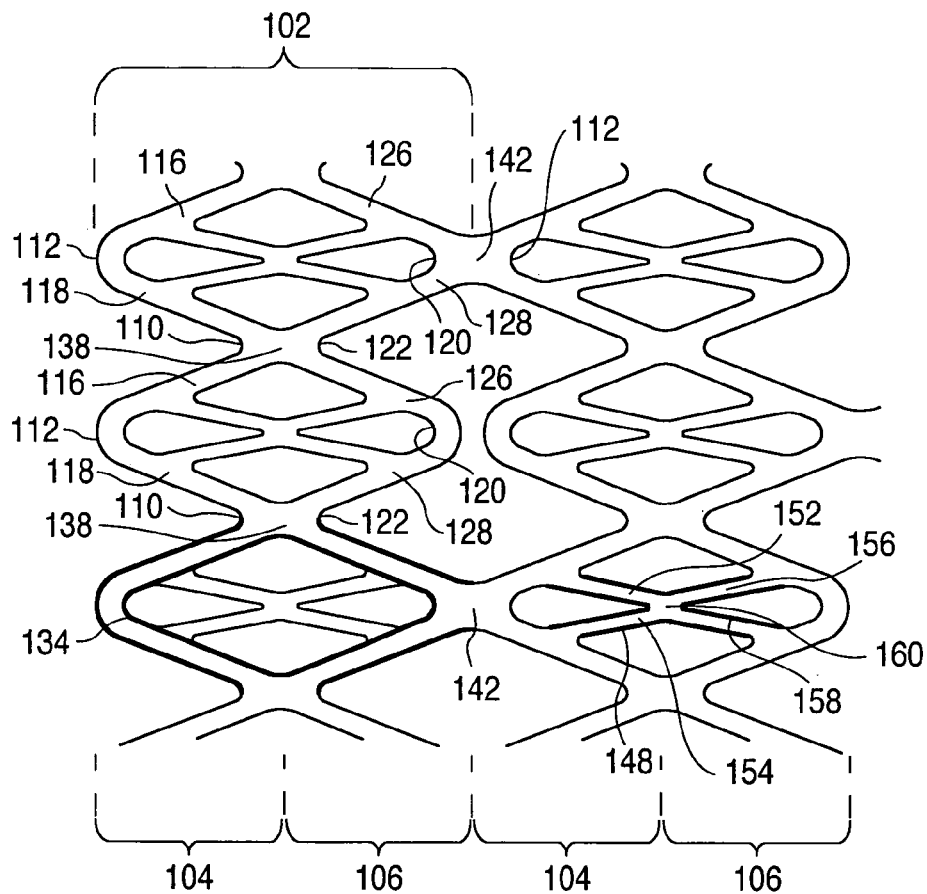
FIG. 6 depicts a portion of the stent pattern in FIG. 5.

As depicted in FIGS. 5 and 6, pairs 102 of radially expandable undulating cylindrical rings 104 and 106 are longitudinally aligned. Rings 104 have peaks 110 and valleys 112 formed by linear bar arms 116 and 118. Rings 106 have peaks 120 and valleys 122 formed by linear bar arms 126 and 128. Pairs 102 of rings are configured such that peaks 110 of ring 104 are connected to valleys 122 at the apices of the peaks and valleys to form a plurality of diamond shaped elements 134 (shown in bold).

Thus, stent 100 may be described as a plurality of radially expandable rings with the rings having a plurality of diamond-shaped elements 134. The rings, as described above, are formed by four linear bar arms, 116, 118, 126 and 128. Adjacent diamond-shaped elements on the ring can be connected at apices 138 of the adjacent elements.

Adjacent cylindrical rings of diamond-shaped elements 134 can be joined by connecting at least one diamond-shaped element to an adjacent diamond-shaped element at longitudinal apices 142 of the diamond-shaped elements. Equivalently, a valley 112 of cylindrical ring 104 of one pair 102 can be connected to a peak 120 of cylindrical ring 106 of another pair 102 at the apices of the peak and valley. Alternatively, adjacent rings can be connected by linear bar arms that connect longitudinal apices of adjacent peaks and valleys.

Embodiments of the stent depicted in FIG. 5 can include any number of diamond-shaped cells or crests along a circumferential direction and rings along the longitudinal axis. Increasing the number of rings may necessitate decreasing the size of the diamond-shaped elements.

Stent 100 can have at least one link between adjacent rings. As shown in FIG. 5, every other pair of longitudinally adjacent diamond-shaped elements 134 is connected at the longitudinal apices of the diamond-shaped elements. In an alternative embodiment, every pair of longitudinally adjacent elements 134 is connected. A stent with every pair connected may tend to have a lower longitudinal flexibility than a stent with every other pair connected.

Stent 100 may also have bar arms that act as support elements within the diamond-shaped elements for increasing the strength of the stent. Stent 100 depicted in FIGS. 5 and 6 have a cross-like element 148 (shown in bold) within diamond-shaped elements 134. Cross-like elements 148 are formed from four linear bar arms 152, 154, 156, and 158. Ends of bar arms 152, 154, 156, and 158 are joined at intersection 160 within at least one diamond-shaped element 134. The other ends of bar arms 152, 154, 156, and 158 are connected to bar arms of diamond-shaped element 134 between two adjacent apices of diamond-shaped element 134, i.e., to arms 116, 118, 126, and 128.

In some embodiments, at least one of the bar arms of the cross-like element may be a different polymeric material than the bar arms of the diamond-shaped element. The cross-like element may have a different modulus than the bar arms of the diamond-shaped element.

An alternative embodiment for support elements within the diamond-shaped elements may include two connecting elements within at least one diamond-shaped element with each element having two ends. The ends of one connecting element may be connected to bar arms of the diamond-shaped element on either side of one longitudinal apex of the diamond-shaped element. The ends of a second connecting element may be connected to bar arms of the diamond-shaped element on either side of a second longitudinal apex of the diamond-shaped element.

Figure 7A:
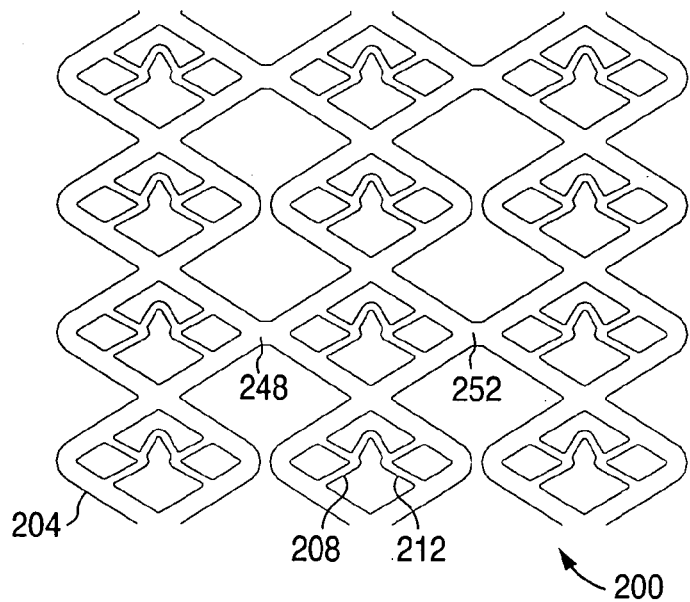
FIG. 7A depicts an alternative stent pattern.
Figure 7B:
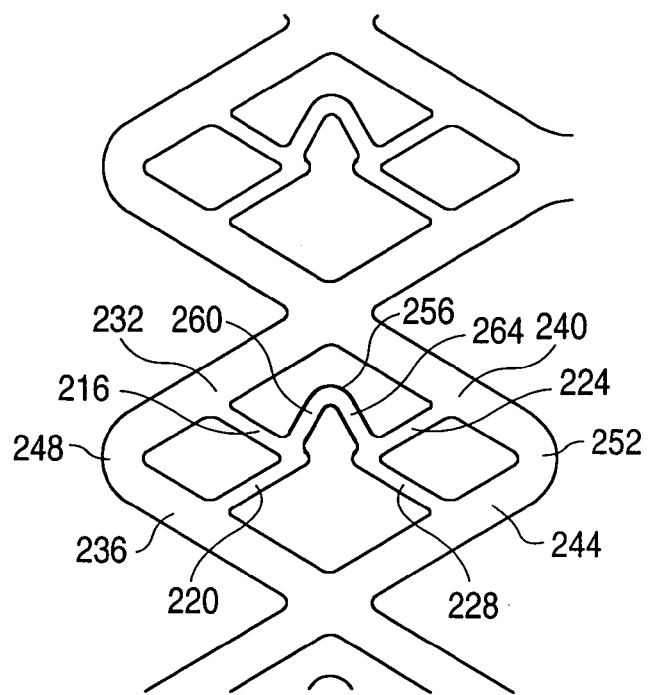
FIG. 7B depicts a portion of the stent pattern in FIG. 7A.

FIG. 7A depicts an alternative embodiment of a stent with support elements within diamond-shaped elements. FIGS. 7A-B depict a stent 200 with a pattern of diamond-shaped elements similar to stent 100 in FIGS. 5 and 6. As depicted in FIGS. 7A and 7B, connecting elements may include v-shaped element 208 and 212 (in bold) within at least one diamond-shaped element 204 (in bold). V-shaped element 208 is formed by short bar arms 216 and 220 and v-shaped element 212 is formed by short bar arms 224 and 228. Short bar arm 216 is connected to bar arm 232 of diamond-shaped element 204 on one side of longitudinal apex 248 and short bar arm 220 is connected to bar arm 236 on another side of longitudinal apex 248. Similarly, short bar arm 224 is connected to bar arm 240 on one side of longitudinal apex 252 and short bar arm 228 is connected to bar arm 244 on another side of longitudinal apex 252. A v-shaped connecting element 256 formed by bar arms 260 and 264 connects apices of v-shaped elements 208 and 212.

In addition, FIG. 7A shows that selected diamond-shaped elements 204 are connected to adjacent rings at both longitudinal apices 248 and 252. Embodiments of stent 100 may also be configured in this manner. Such a configuration may facilitate plastic deformation in support elements at an earlier stage.

The support structure including v-shaped elements 208, 212, and 256 may be advantageous because the v-shaped elements 208 and 212 can have freedom to move (e.g., expand, twist, etc). These arms can be collapsed to minimize a profile yet can be expanded to the desired diameter.

As indicated above, expansion of a stent tends to result in substantial deformation in localized portions of the stent pattern. Such deformation can result in strain induced crystallization which may tend to increase the strength and modulus of these portions. When a stent having a pattern such as those depicted in FIGS. 5-6 and 7A-B is expanded, the diamond shaped elements tend to become narrower along the longitudinal axis and longer along the circumferential direction.

Figure 8A:
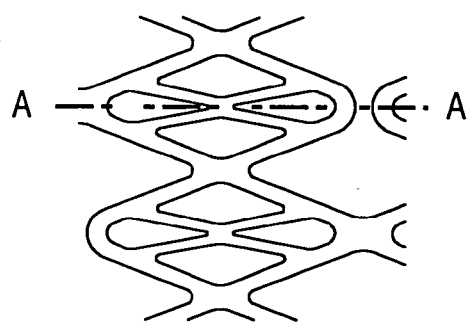
FIG. 8A depicts a portion of the stent pattern of FIG. 5 in an unexpanded state.

FIG. 8A depicts a portion of the stent 100 from FIG. 5 that is not expanded and FIG. 8B depicts the portion when the stent is expanded. As above, line A-A represents the longitudinal axis of the stent. As shown by FIG. 8B, the diamond-shaped region becomes narrower along line A-A and longer along the circumferential direction. Substantial local deformation tends to occur in regions 280, 281, 282, and 283, where bar arms bend. Deformation occurs due to a change in angle between, e.g., bar arms 116 and 126; bar arms 118 and 128; 116 and 118; and 126 and 128. Plastic deformation in regions 280-283 tends to increase the radial strength of the stent and reduces Tecoil. Additionally, permanent deformation in regions 280-283 locks in the expanded configuration, also reducing recoil.

Figure 8C:
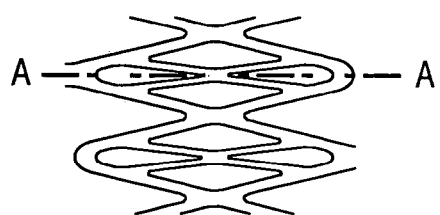
FIG. 8C depicts a portion of the stent pattern of FIG. 5 in a crimped state.

In a similar manner, FIG. 8C depicts the portion when the stent is crimped. As shown by FIG. 8C, the diamond-shaped region becomes wider along line A-A and longer along the circumferential direction.

Furthermore, cross-like elements in the diamond-shaped regions also tend to increase the radial strength of the stent pattern. As stent 100 expands, bar arms 152, 154, 156, and 158 of the cross-like elements tend to elongate or stretch along their lengths. Angles 284 and 288 between adjacent bar arms of the cross-like elements also increase as the stent expands. Therefore, the circumferential alignment of bar arms 152, 154, 156, and 158 tends to increase as the stent expands. Plastic deformation of bar arms 152, 154, 156, and 158 of the stent increases their strength and modulus and locks in the expanded configuration. Therefore, bar arms 152, 154, 156, and 158 also tend to increase the radial strength of the stent upon expansion.

Additionally, since bar arms 152, 154, 156, and 158 are shorter, they tend to plastically deform prior to the bar arms of the diamond shaped elements, specifically region 280-283. As indicated above, the smaller the mass of a bar arm, the more it deforms under an applied stress. Therefore, the bar arms of the cross-like elements may act as columns that provide resistance against recoil and inward radial forces.

Also, the width of the bar arms of cross-like elements may also be varied to control the amount of plastic deformation in the bar arms. As indicated above, the thinner the bar arm, the more it deforms under an applied stress.

FIG. 9A depicts a portion of stent 200 from FIG. 7A that is not expanded and FIG. 9B depicts the portion when it is expanded. As above, line A-A represents the longitudinal axis of the stent. As stent 200 expands, bar arms 216 and 220 of v-shaped element 208 and bar arms 224 and 228 of v-shaped element 212 tend to elongate or stretch along their lengths. Angles 292 and 296 also increase as the stent expands. Angle 300 may increase or decrease. The circumferential alignment of the bar arms 216 and 220 of v-shaped element 208 and bar arms 224 and 228 of v-shaped element 212 may tend to be greater than bar arms 232, 236, 240 and 244. Plastic deformation of the bar arms of v-shaped elements 208 and 212 of the stent increases their strength and modulus and helps to lock in the expanded configuration. Therefore, the bar arms of v-shaped elements 208 and 212 also tend to increase the radial strength of the stent upon expansion.

The stent patterns disclosed herein are not limited in application to stents. The pattern may be applied to implantable medical devices including, but not limited to, self-expandable stents, balloon-expandable stents, stent-grafts, and vascular grafts.

Stent patterns for polymeric stents may be formed from a polymeric tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. The stent may be formed by injection molding of a thermoplastic or reaction injection molding of a thermoset polymeric material.

Polymer tubes used for fabricating stents may be formed by various methods. These include, but are not limited to extrusion or injection molding. A tube used for fabricating a stent may be cylindrical or substantially cylindrical in shape. Conventionally extruded tubes tend to possess no or substantially no radial orientation or, equivalently, polymer chain alignment in the circumferential direction.

In some embodiments, the diameter of the polymer tube prior to fabrication of an implantable medical device may be between about 0.2 mm and about 5.0 mm, or more narrowly between about 1 mm and about 3 mm. In an embodiment, the length of the stents described herein may be between about 7 mm and about 9 mm, or more narrowly, between about 7.8 and about 8.2 mm.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

EXAMPLES

The embodiments of the present invention will be illustrated by the following set forth examples. All parameters and data are not to be construed to unduly limit the scope of the embodiments of the invention.

Stents were evaluated using flat plate compression and recoil tests. The radial strength is measure of the amount of force necessary to compress a stent a particular fraction of its original diameter, e.g., 10%, 25%, or 50%. All stents were fabricated from 100% poly(L-lactic acid) (PLA) tubing, unless otherwise noted.

Recoil is defined with respect to the inside diameter (ID) of the stent: (ID of stent with balloon inflated—ID of stent with balloon deflated)/ID of stent with balloon inflated. The crimp profile corresponds to the outside diameter of a stent crimped on a catheter.

Example 1

Figure 10:
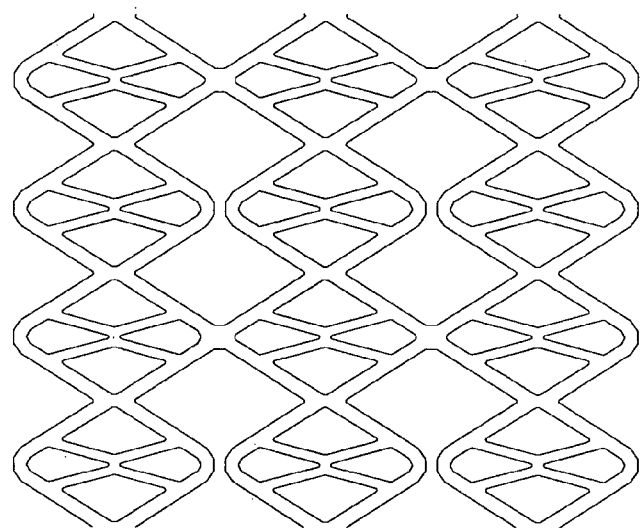
FIG. 10 depicts a stent pattern of example 1.

FIG. 10 depicts a diagram of the stent of example 1. The pattern has 4 crests along the circumference and adjacent rings are linked by two connections on each diamond-shaped element that is connected to an adjacent ring (4-crest, 2 link design).

The pattern in FIG. 10 may be more desirable than the pattern depicted in FIG. 5 (5-crest, 2-link design) because it has a smaller radial profile. In addition, the width of the struts is smaller which facilitates the onset of plastic deformation.

Figure 11A:
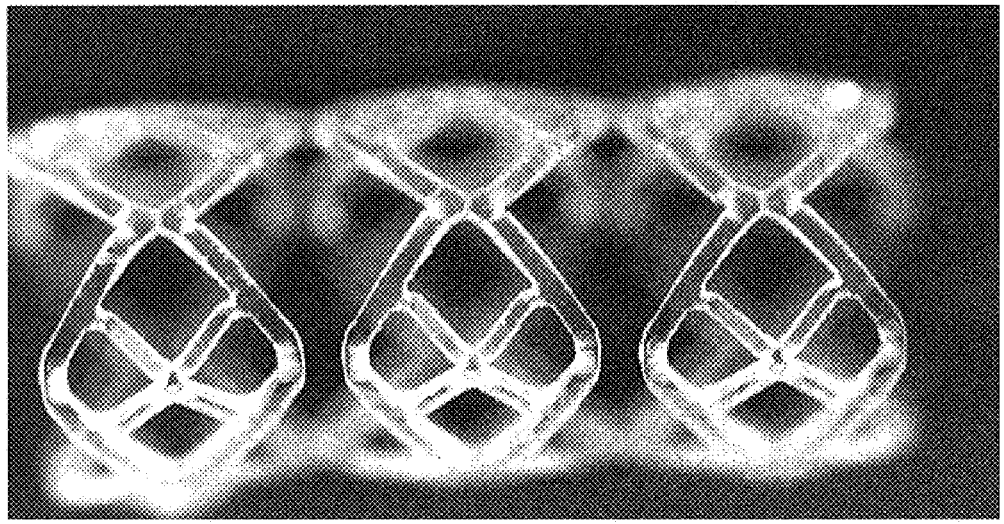
FIG. 11A-B depicts optical micrographs of the stent of example 1 in an expanded state.
Figure 11B:
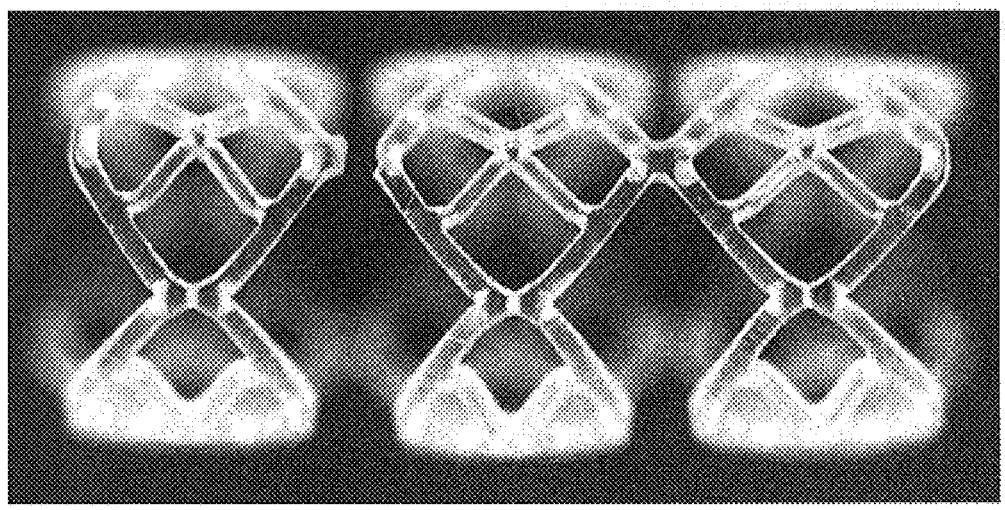

The inner radii of the diamonds are also smaller to reduce the likelihood of cracking upon expansion. Decreasing the inner radius tends to concentrate stress which allows a deformed region to reach plastic deformation sooner. The test results are shown in Table 1. FIGS. 11A-B depicts optical micrographs of the stent of example 1 in an expanded state.

TABLE 1

Test results for stent of example 1.

| | |
|---|---|
| Average % recoil: | 11% |
| Average radial strength | |
| 10% | 0.087 N/mm |
| 25% | 0.149 N/mm |
| 50% | 0.252 N/mm |
| Average crimp profile | 0.0642 in |

Example 2

Figure 12:
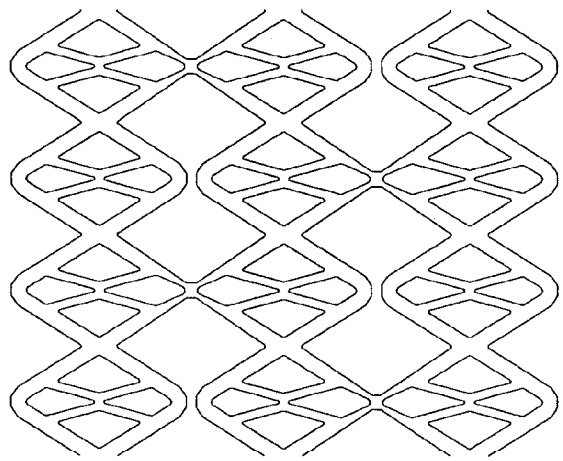
FIG. 12 depicts a stent pattern of example 2.

FIG. 12 depicts a diagram of the stent of example 2. This pattern is a 4-crest, 2-link design. As shown in FIG. 12, the width of the bar arms at and adjacent the links between rings or connected crests is reduced to facilitate deformation. In general, unconnected crests tend to experience a higher degree of deformation than connected crests, in a pattern such as in FIG. 5, since the mass of the connected crests is higher. The high deformation in the unconnected crests can lead to cracking. Thus, reducing the mass at the connected crests tends to increase the deformation at these crests which redistributes or balances the deformation between connected and unconnected crests.

Figure 13A:
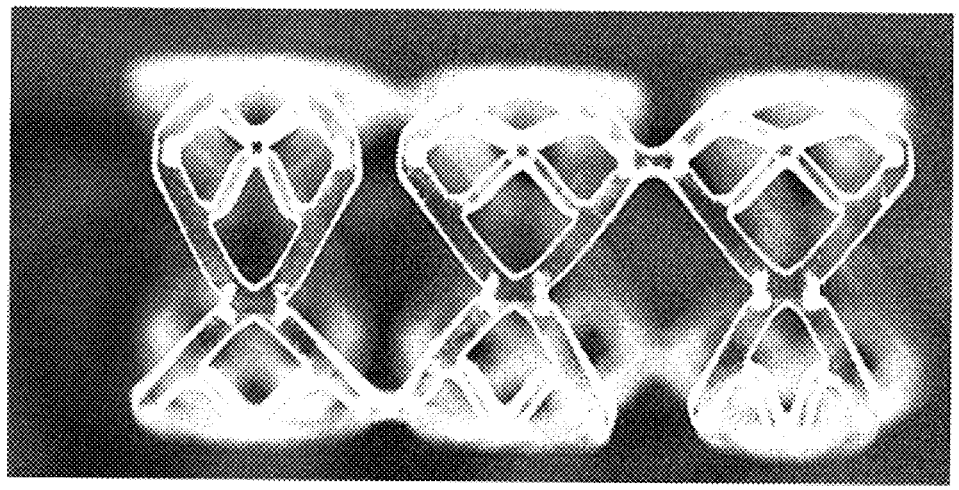
FIG. 13A-B depicts optical micrographs of the stent of example 2 in an expanded state.
Figure 13B:
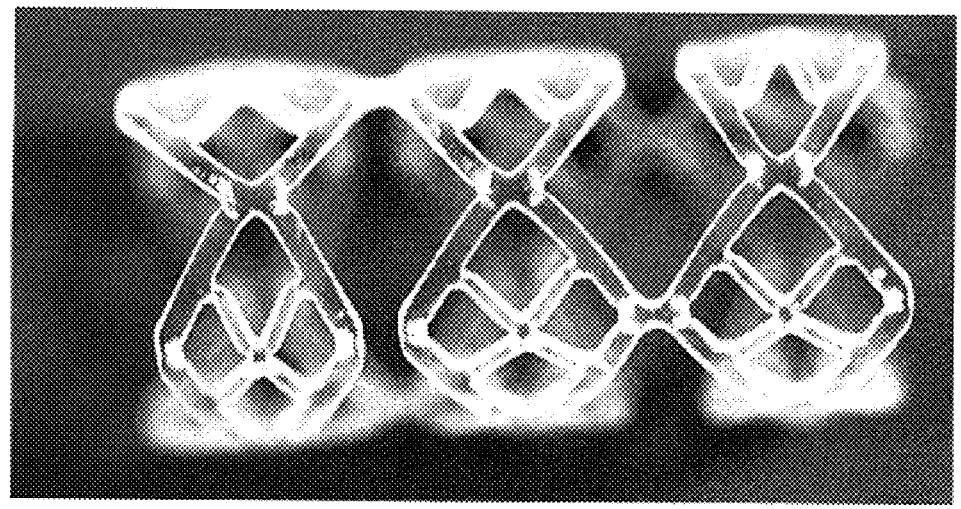

In addition, diamond-shaped elements only have one link between rings. This adjustment was made also to reduce or prevent cracking at the unconnected crests. The test results are shown in Table 2. FIGS. 13A-B depicts optical micrographs of the stent of example 2 in an expanded state.

TABLE 2

Test results for stent of example 2.

| | |
|---|---|
| Average % recoil: | 8.7% |
| Average radial strength | |
| 10% | 0.072 N/mm |
| 25% | 0.134 N/mm |

TABLE 2-continued

Test results for stent of example 2.

| | |
|---|---|
| 50% | 0.236 N/mm |
| Average crimp profile | 0.054 in |

Examples 3-6

The stent patterns of examples 3-6 shown in FIGS. 14-17, respectively, are 4-crest, 2-link designs. As shown by FIGS. 14-17, the stent designs of examples 3-6 have a longer connector between rings than designs in the other examples. The width of the bar arms at and adjacent the links between rings is also reduced to facilitate deformation. The longer connecter tends to decouple the deformation at the bends or vertices that are connected and results in a decrease in mass at the bends or vertices. Therefore, the regions at the decoupled bends have a greater tendency to deform and reach plastic deformation sooner.

Figure 14:
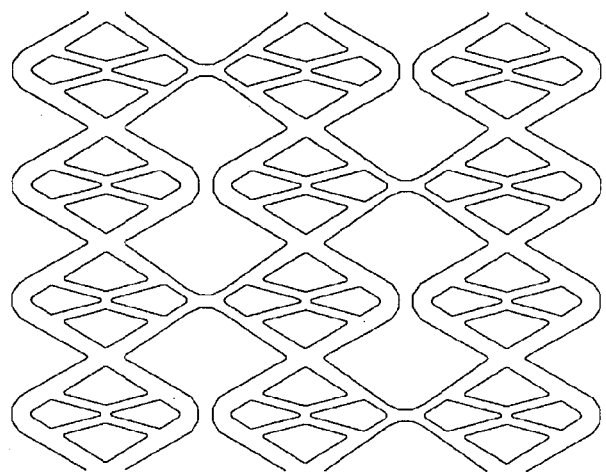
FIG. 14 depicts a stent pattern of example 3.

In the test of example 4, FIG. 14, stent struts broke at the connector between rings.

Figure 15:
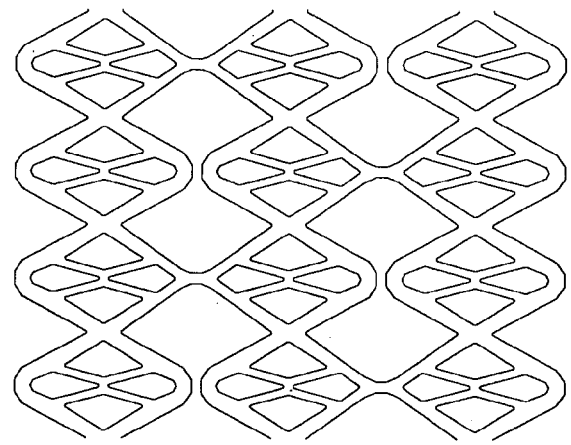
FIG. 15 depicts a stent pattern of example 4.
Figure 16:
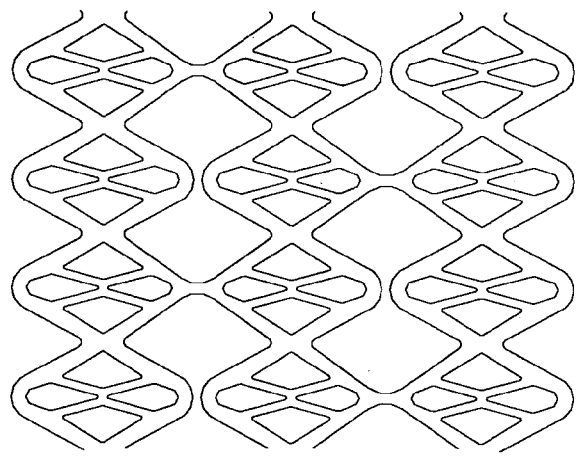
FIG. 16 depicts a stent pattern of example 5.
Figure 17:
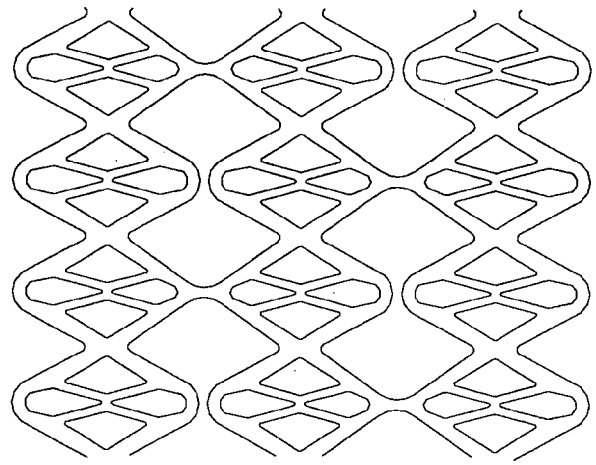
FIG. 17 depicts a stent pattern of example 6.

The stent of example 5, FIG. 15, has a larger inner radius at the diamonds. Two stents of example 5 had no struts broken and one had four broken struts along the unconnected crests.

The stent of example 6 has a larger inner radius in the diamonds. Two stent with the pattern of example 6 were tested: one composed of 100% PLA and another that was 80% PLA/20% poly(D, L lactic acid). The former had had broken struts and the latter did not have any broken struts.

Figure 18A:
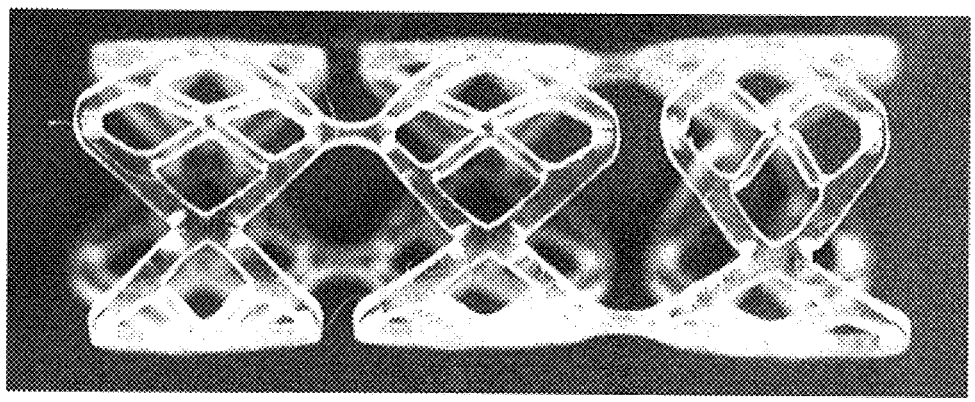
FIG. 18A-B depicts optical micrographs of the stent of examples 3-6 in an expanded state.
Figure 18B:
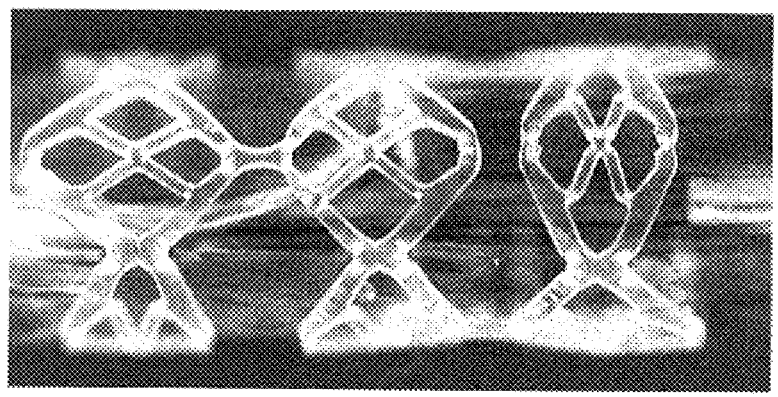

No quantitative results for recoil, radial strength, and crimp profile are available for examples 3-6 since the stents could not be crimped. FIGS. 18A-B depicts optical micrographs of the stents of examples 3-6 in an expanded state.

Example 7

Figure 20:
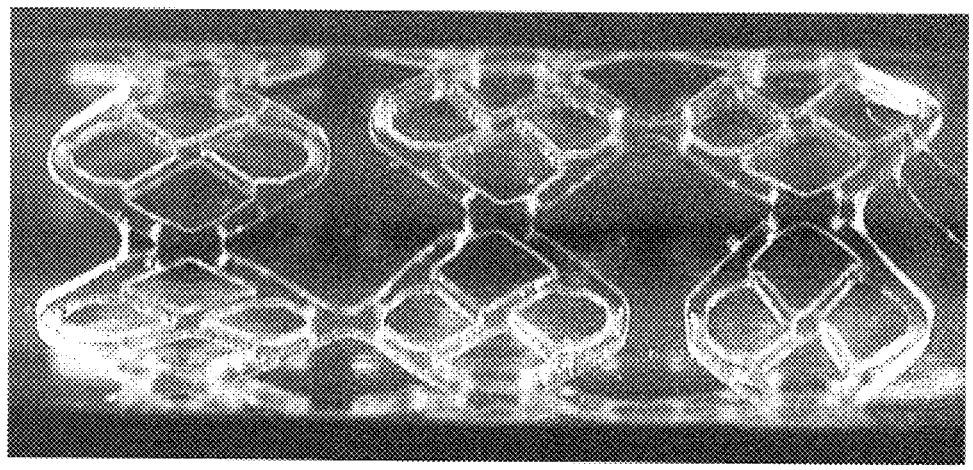
FIG. 20 depicts an optical micrograph of the stent of example 7 in an expanded state.
Figure 19:
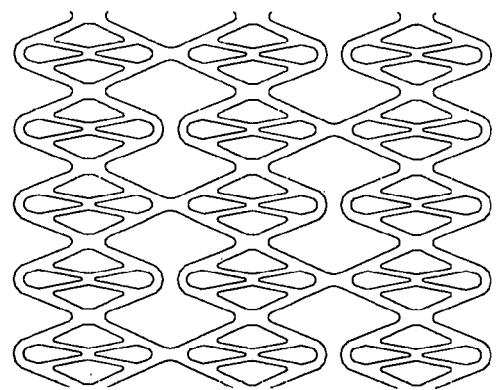
FIG. 19 depicts a stent pattern of example 7.

FIG. 19 depicts a diagram of the stent of example 7. Example 7 is a stent with a 5-crest design with three links between one pair of rings and two links between another ring. The additional crest in the pattern tends to reduce the amount of shortening and cracking. In the test of the stent of example 7, stent shortening of approximately 18% was observed. In addition, diamond-shaped elements only have one link between rings. The test results are shown in Table 3. FIG. 20 depicts an optical micrograph of the stent of example 7 in an expanded state.

TABLE 3

Test results for stent of example 7.

| | |
|---|---|
| Average % recoil: | 10.6% |
| Average radial strength | |
| 10% | 0.034 N/mm |
| 25% | 0.056 N/mm |
| 50% | 0.069 N/mm |
| Average crimp profile | N/A |

Example 8

Figure 21:
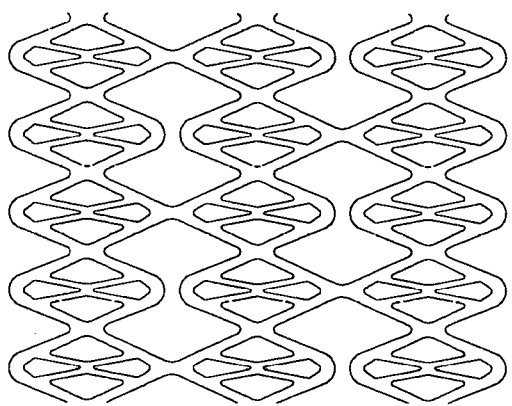
FIG. 21 depicts a stent pattern of example 8.
Figure 22:
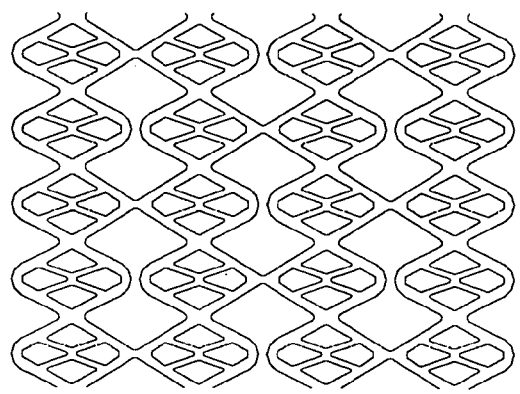
FIG. 22 depicts a stent pattern of example 9.

FIG. 21 depicts a diagram of the stent of example 8. The pattern of example 8 is similar to example 7. The width of the unconnected crest is increased over that of example 7 to reduce recoil. The greater width also redistributes stress to the connected crests which facilitates plastic deformation at these crests. Example 8 was not tested.

Example 9

FIG. 21 depicts a diagram of the stent of example 9. This pattern is a 5-crest design with four cylindrical rings of diamond-shaped elements. The two pairs of rings have three links and one pair of rings in the middle has one pair of links. The size of the diamond-shaped elements is reduced to accommodate the additional ring. The additional ring may reduce the amount of recoil in a smaller diamond-shaped element since plastic deformation may be more readily induced at the ends of the diamond-shaped elements.

Example 10

FIG. 7A depicts the stent of example 8. The test results are shown in Table 4.

Figure 23A:
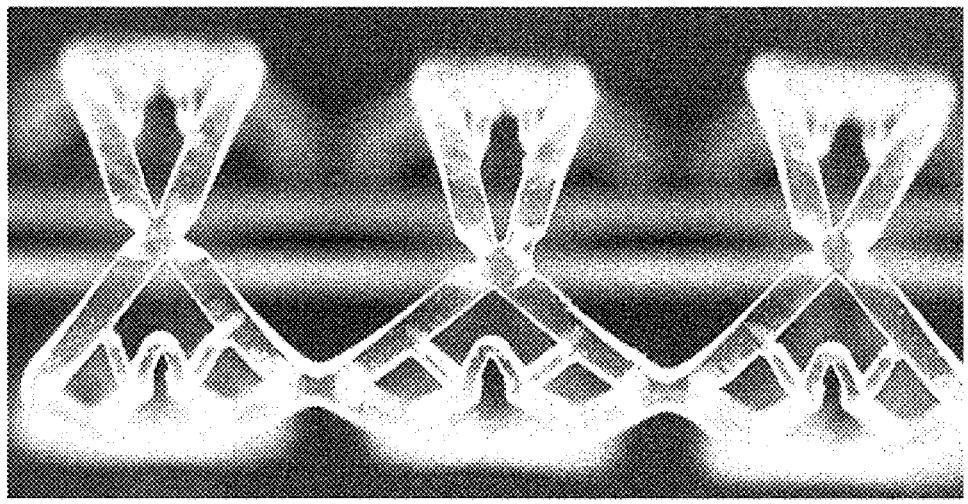
FIG. 23A-B depicts an optical micrographs of the stent of example 10 in an expanded state.
Figure 23B:
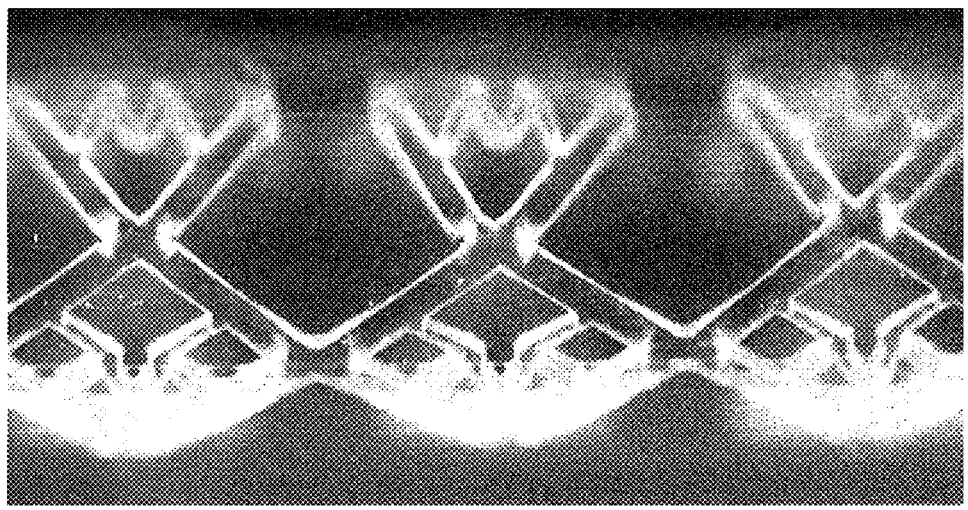

FIGS. 23A-B depict optical micrographs of the stent of example 10 in an expanded state.

TABLE 4

Test results for stent of example 10.

| Average % recoil: | 11% |
|---|---|
| Average radial strength | |
| 10% | 0.087 N/mm |
| 25% | 0.149 N/mm |
| 50% | 0.252 N/mm |
| Average crimp profile | 0.0642 in |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A radially expandable intravascular stent for implanting in a bodily lumen, comprising:
a plurality of radially expandable cylindrical rings that are longitudinally aligned, each ring comprising:
a first delivery diameter and a second implanted diameter; and
a plurality of diamond-shaped elements formed by four linear bar arms, wherein adjacent elements on the ring are connected at apices of the adjacent elements,
a cross-like element comprising four linear bar arms interconnected within at least one diamond-shaped element, wherein one end of each bar arm of the cross-like element is connected to one of the bar arms of the at least one diamond-shaped element between two adjacent apices of the at least one diamond-shaped element; and
at least one link between adjacent rings, wherein the at least one link connects longitudinal apices of adjacent diamond-shaped elements of adjacent rings.

2. The stent of claim 1, wherein the stent comprises a biostable polymer and/or a bioabsorbable polymer.

3. The stent of claim 1, wherein the at least one link between adjacent rings comprise a connection at the longitudinal apices of the adjacent diamond-shaped elements.

4. The stent of claim 1, wherein the at least one link between adjacent rings comprise a linear bar arm.

5. The stent of claim 1, wherein at least one of the bar arms of a cross-like element is configured to plastically deform along a longitudinal axis of the bar arm when the stent expands.

6. The stent of claim 1, wherein at least one of the bar arms of the diamond-shaped element is longer than the bar arms of the cross-like element.

7. The stent of claim 1, wherein a width of at least one of the bar arms of the diamond-shaped element is larger than the bar arms of the cross-like element.

8. The stent of claim 1, wherein at least one of the bar arms of the cross-like element comprise a different polymeric material than the bar arms of the diamond-shaped element.

9. The stent of claim 1, wherein at least one of the bar arms of the cross-like element comprise a higher modulus material than the bar arms of the diamond-shaped regions.

10. The stent of claim 1, wherein at least one of the bar arms of the cross-like element comprise a lower modulus material than the bar arms of the diamond-shaped elements.

11. A radially expandable intravascular stent for implanting in a bodily lumen, comprising:
a plurality of pairs of radially expandable undulating cylindrical rings that are longitudinally aligned comprising peaks and valleys formed by linear bar arms, wherein the pairs of rings are configured such that the peaks of one pair are connected to the valleys of the other pair at apices of the peaks and valleys to form a plurality of diamond shaped regions;
at least one link between adjacent rings, wherein the at least one link connects a peak on one ring to an adjacent valley on an adjacent ring; and
a cross-like element comprising four linear bar arms interconnected within at least one diamond-shaped element, wherein one end of each bar arm of the cross-like element is connected to one of the linear bar arms of the rings between a peak and a valley of the ring and another end of each bar arm interconnected to ends of the bar arms of the cross-like element.

12. The stent of claim 11, wherein the stent comprises a biostable polymer and/or a bioabsorbable polymer.

13. The stent of claim 11, wherein the at least one link between adjacent rings comprise a connection of the peak on one ring to the adjacent valley at the apices of the peak and the adjacent valley.

14. The stent of claim 11, wherein the at least one link between adjacent rings comprise a linear bar arm.

15. The stent of claim 11, wherein at least one of the bar arms of a cross-like element are configured to plastically deform along a longitudinal axis of the bar arm when the stent expands.

16. The stent of claim 11, wherein at least one of the bar arms of the pairs of cylindrical rings are longer than the bar arms of the cross-like element.

17. The stent of claim 11, wherein a width of each of at least one of the bar arms of the pairs of cylindrical rings is larger than the bar arms of the cross-like element.

18. A radially expandable intravascular stent for implanting in a bodiy lumen, comprising:
a plurality of radially expandable cylindrical rings that are longitudinally aligned, each ring comprising:
a first delivery diameter and a second implanted diameter; and
a plurality of diamond-shaped elements formed by four linear bar arms, wherein adjacent elements on the ring are connected at apices of the adjacent elements;

at least one link between adjacent rings, wherein the at least one link connects longitudinal apices of adjacent diamond-shaped elements of adjacent rings;

two v-shaped elements formed by two short bar arms within at least one diamond-shaped element, ends of the short bar arms of one v-shaped element are connected to bar arms of the diamond-shaped element on either side of one longitudinal apex of the diamond-shaped element, and ends the short bar arms of a second v-shaped element are connected to bar arms of the diamond-shaped element on either side of a second longitudinal apex of the diamond-shaped element; and a connecting bar arm within at least one diamond-shaped element connecting the apices of the two v-shaped elements.

19. A radially expandable intravascular stent for implanting in a bodily lumen, comprising:

a plurality of pairs of radially expandable undulating cylindrical rings that are longitudinally aligned comprising peaks and valleys formed by linear bar arms, wherein the pairs of rings are configured such that the peaks of one pair are connected to the valleys of the other pair at apices of the peaks and valleys to form a plurality of diamond shaped regions;

at least one link between adjacent rings, wherein the at least one link connects a peak on one ring to an adjacent valley on an adjacent ring;

two v-shaped elements formed by two short bar arms within at least one diamond-shaped element, ends of the short bar arms of one v-shaped element are connected to bar arms of the diamond-shaped element on either side of one longitudinal apex of the diamond-shaped element, and ends the short bar arms of a second v-shaped element are connected to bar arms of the diamond-shaped element on either side of a second longitudinal apex of the diamond-shaped element; and a connecting bar arm within at least one diamond-shaped element connecting the apices of the two v-shaped elements.

20. A radially expandable intravascular stent for implanting in a bodily lumen, comprising:

a plurality of radially expandable cylindrical rings that are longitudinally aligned, each ring comprising:

a first delivery diameter and a second implanted diameter; and a plurality of diamond-shaped elements formed by four linear bar arms, wherein adjacent elements on the ring are connected at apices of the adjacent elements;

two connecting elements within at least one diamond-shaped element with each element having two ends, the ends of one connecting element are connected to bar arms of the diamond-shaped element on either side of one longitudinal apex of the diamond-shaped element, and the ends of a second connecting element are connected to bar arms of the diamond-shaped element on either side of a second longitudinal apex of the diamond-shaped element;

a connecting bar arm within at least one diamond-shaped element connecting the two connecting elements; and at least one link between adjacent rings, wherein the at least one link connects longitudinal apices of adjacent diamond-shaped elements of adjacent rings.

21. The stent of claim 20, wherein the first connecting element comprises a first v-shaped bar arm, the ends of the first v-shaped bar arm are connected to bar arms of the diamond-shaped element on either side of one longitudinal apex of the diamond-shaped element, and wherein the second connecting element comprises a second v-shaped bar arm, the ends of the second v-shaped bar arm are connected to bar arms of the diamond-shaped element on either side of a second longitudinal apex of the diamond-shaped element.

* * * * *